(12) United States Patent
Adler et al.

(10) Patent No.: US 8,692,874 B2
(45) Date of Patent: Apr. 8, 2014

(54) IMAGING SYSTEMS AND METHODS, PARTICULARLY FOR USE WITH MEDICAL INSTRUMENT USED IN OPEN SURGERY

(75) Inventors: Doron Adler, Haifa (IL); Shai Finkman, Haifa (IL); Oded Beckermus, Kiryat Ata (IL); Oren Beckermus, Tel-Aviv (IL)

(73) Assignee: Gyrus ACMI, Inc., Southborough, MA (US)

( * ) Notice: Subject to any disclaimer, the term of this patent is extended or adjusted under 35 U.S.C. 154(b) by 1178 days.

(21) Appl. No.: 12/104,406

(22) Filed: Apr. 16, 2008

(65) Prior Publication Data

US 2009/0051763 A1    Feb. 26, 2009

Related U.S. Application Data

(60) Provisional application No. 60/912,337, filed on Apr. 17, 2007, provisional application No. 61/016,557, filed on Dec. 24, 2007.

(51) Int. Cl.
    *A62B 1/04*        (2006.01)

(52) U.S. Cl.
    USPC ............... 348/65; 359/611; 396/17; 600/160

(58) Field of Classification Search
    USPC .......... 348/65, 73; 359/611; 396/17; 600/160
    See application file for complete search history.

(56) References Cited

U.S. PATENT DOCUMENTS

| | | | |
|---|---|---|---|
| 4,905,670 A | | 3/1990 | Adair |
| 5,009,481 A | * | 4/1991 | Kinoshita et al. ............... 385/33 |
| 5,325,847 A | | 7/1994 | Matsuno |
| 5,399,231 A | | 3/1995 | McCarthy |
| 5,569,157 A | | 10/1996 | Nakazawa et al. |
| 5,570,237 A | | 10/1996 | Sato |
| 5,667,473 A | | 9/1997 | Finn et al. |
| 5,667,478 A | | 9/1997 | McFarlin et al. |
| 5,685,823 A | | 11/1997 | Ito et al. |
| 5,700,236 A | | 12/1997 | Sauer et al. |
| 5,735,792 A | | 4/1998 | Vanden Hoek et al. |
| 5,743,731 A | * | 4/1998 | Lares et al. ..................... 433/29 |

(Continued)

FOREIGN PATENT DOCUMENTS

| | | |
|---|---|---|
| DE | AS1122738 | 1/1962 |
| DE | 4133493 | 4/1992 |

(Continued)

OTHER PUBLICATIONS

International Search Report and Written Opinion dated Jul. 26, 2007 for PCTUS2005045469, filed Dec. 13, 2005, 15 pages.

(Continued)

*Primary Examiner* — Oleg Survillo
(74) *Attorney, Agent, or Firm* — The Dobrusin Law Firm, PC

(57) ABSTRACT

An electronic imaging apparatus (and related methods of manufacture and use), comprising: a chassis, having an open cylindrical groove formed therein; an image sensor assembly mounted in the chassis, the image sensor assembly comprising an electronic image sensor; a plurality of lenses, which are fitted into the groove in respective positions so as to form an image on the image sensor; and a cover, which closes over the image sensor assembly and the lenses in the chassis. The imaging system is particularly suitable as a compact imaging systems for use on instruments for open surgery.

20 Claims, 7 Drawing Sheets

(56) References Cited

U.S. PATENT DOCUMENTS

| | | | |
|---|---|---|---|
| 5,854,711 A * | 12/1998 | Kaneda | 359/697 |
| 5,868,664 A | 2/1999 | Speier et al. | |
| 5,871,440 A | 2/1999 | Okada | |
| 5,961,445 A | 10/1999 | Chikama | |
| 5,978,608 A * | 11/1999 | Tasaka et al. | 396/315 |
| 6,030,339 A | 2/2000 | Tatsuno et al. | |
| 6,063,023 A | 5/2000 | Sakiyama et al. | |
| 6,080,101 A | 6/2000 | Tatsuno et al. | |
| 6,122,115 A | 9/2000 | Plummer et al. | |
| 6,184,923 B1 | 2/2001 | Miyazaki | |
| 6,371,973 B1 * | 4/2002 | Tepper | 606/205 |
| 6,390,972 B1 | 5/2002 | Speier et al. | |
| 6,419,626 B1 * | 7/2002 | Yoon | 600/109 |
| 6,428,180 B1 | 8/2002 | Karram et al. | |
| 6,485,413 B1 | 11/2002 | Boppart et al. | |
| 6,547,722 B1 | 4/2003 | Higuma et al. | |
| 6,554,767 B2 | 4/2003 | Tanaka | |
| 6,565,505 B2 | 5/2003 | Ishibiki | |
| 6,572,537 B2 | 6/2003 | Futatsugi et al. | |
| 6,589,165 B2 | 7/2003 | Bodor et al. | |
| 6,605,035 B2 | 8/2003 | Ando et al. | |
| 6,641,530 B2 * | 11/2003 | Mitsumori | 600/167 |
| 6,695,775 B2 | 2/2004 | Watanabe et al. | |
| 6,716,161 B2 | 4/2004 | Higuma et al. | |
| 6,776,328 B2 | 8/2004 | Rice et al. | |
| 6,805,664 B2 | 10/2004 | Doyle et al. | |
| 6,937,406 B2 * | 8/2005 | Matsushima et al. | 359/819 |
| 6,955,644 B2 | 10/2005 | Forkey et al. | |
| 7,300,397 B2 | 11/2007 | Adler et al. | |
| 7,410,462 B2 * | 8/2008 | Navok et al. | 600/133 |
| 7,549,958 B2 | 6/2009 | Hirata | |
| 2001/0016679 A1 | 8/2001 | Futatsugi et al. | |
| 2004/0019255 A1 | 1/2004 | Sakiyama | |
| 2005/0250983 A1 | 11/2005 | Tremaglio et al. | |
| 2006/0004256 A1 | 1/2006 | Gilad et al. | |
| 2006/0108594 A1 * | 5/2006 | Iwasaki et al. | 257/98 |
| 2006/0222300 A1 | 10/2006 | Frenzel et al. | |
| 2006/0253004 A1 | 11/2006 | Frisch et al. | |
| 2007/0276182 A1 | 11/2007 | Adler et al. | |
| 2008/0104622 A1 * | 5/2008 | Yabe et al. | 720/681 |
| 2008/0300463 A1 | 12/2008 | Navok et al. | |
| 2010/0228261 A1 * | 9/2010 | Feingold et al. | 606/107 |
| 2011/0290883 A1 * | 12/2011 | Kotlarsky et al. | 235/462.11 |
| 2012/0063761 A1 * | 3/2012 | Tang et al. | 396/133 |

FOREIGN PATENT DOCUMENTS

| | | |
|---|---|---|
| DE | 20104874 | 8/2001 |
| DE | 10252446 | 5/2004 |
| DE | 10344768 | 8/2005 |
| GB | 906278 | 8/1960 |
| JP | 60-009591 | 1/1985 |
| JP | 61-002834 | 1/1986 |
| JP | 62-066220 | 3/1987 |
| JP | 62174955 | 7/1987 |
| JP | 01-136629 A | 5/1989 |
| JP | 3-223707 | 10/1991 |
| JP | 04-295327 | 10/1992 |
| JP | 04-335611 | 11/1992 |
| JP | 07-047050 | 2/1995 |
| JP | 07-093463 | 4/1995 |
| JP | 08-065579 | 3/1996 |
| JP | 09-323174 | 12/1997 |
| JP | 10-210344 | 8/1998 |
| JP | 10-262927 | 10/1998 |
| JP | 11-305146 | 11/1999 |
| JP | 2000024923 | 1/2000 |
| JP | 2000-120997 | 4/2000 |
| JP | 2000100988 | 4/2000 |
| JP | 2000-262458 | 9/2000 |
| JP | 2000-287913 | 10/2000 |
| JP | 2000-321394 | 11/2000 |
| JP | 2001078956 | 3/2001 |
| JP | 2001-212075 | 8/2001 |
| JP | 2005-70505 | 3/2005 |
| WO | WO0182666 A1 | 11/2001 |
| WO | WO2004036266 A2 | 4/2004 |
| WO | WO2006066022 A2 | 6/2006 |
| WO | WO2007113815 | 10/2007 |

OTHER PUBLICATIONS

U.S. Patent and Trademark Office action dated Aug. 10, 2007 for U.S. Appl. No. 11/300,068, now U.S. Patent No. 7,410,462; 11 pages.

U.S. Patent and Trademark Office final action dated Mar. 11, 2008 for U.S. Appl. No. 11/300,068, now U.S. Pat. No. 7,410,462; 14 pages.

International Search Report dated Jul. 9, 2004 for PCTUS2003032975, filed Oct. 17, 2003, 15 pages.

English translation of German Patent Office Examination Report issued for corresponding German Patent Application No. 10393045.0; 8 pages.

Office action from the Patent Office of Germany dated Feb. 2, 2010 for related German patent application No. 102008018922.7, including informal English translation, 8 pages total.

Japanese Office Action dated Feb. 16, 2010 for related Japanese patent application No. 2007-546902; an informal English summary of the Report provided by the Japanese agent is included; 5 pages total.

United States Non-Final Office Action dated Jun. 15, 2010 for related U.S. Appl. No. 11/109,024; 6 pages total.

United States Final Office Action dated Dec. 8, 2009 for related U.S. Appl. No. 11/109,024; 8 pages total.

United States Non-Final Office Action dated Jun. 5, 2009 for related U.S. Appl. No. 11/109,024; 7 pages total.

Office Action dated Mar. 1, 2011, and issued by the Patent Office of Japan in Japanese Patent Application No. 2008-107401; (in the Japanese language); 3 pages.

Office Action dated Mar. 1, 2011, and issued by the Patent Office of Japan in Japanese Patent Application No. 2008-107400; (in the Japanese language); 3 pages.

Office Action dated May 12, 2010, and issued by the German Patent and Trademark Office in German Patent Application No. 102008018932.4-35 (in the German language); 5 pages—English language translation of Office Action included—5 pages.

German Examination Report dated Apr. 30, 2010 for related German patent application No. 11205002972.7; an informal English translation of the Report provided by the German agent is included; 8 pages total.

* cited by examiner

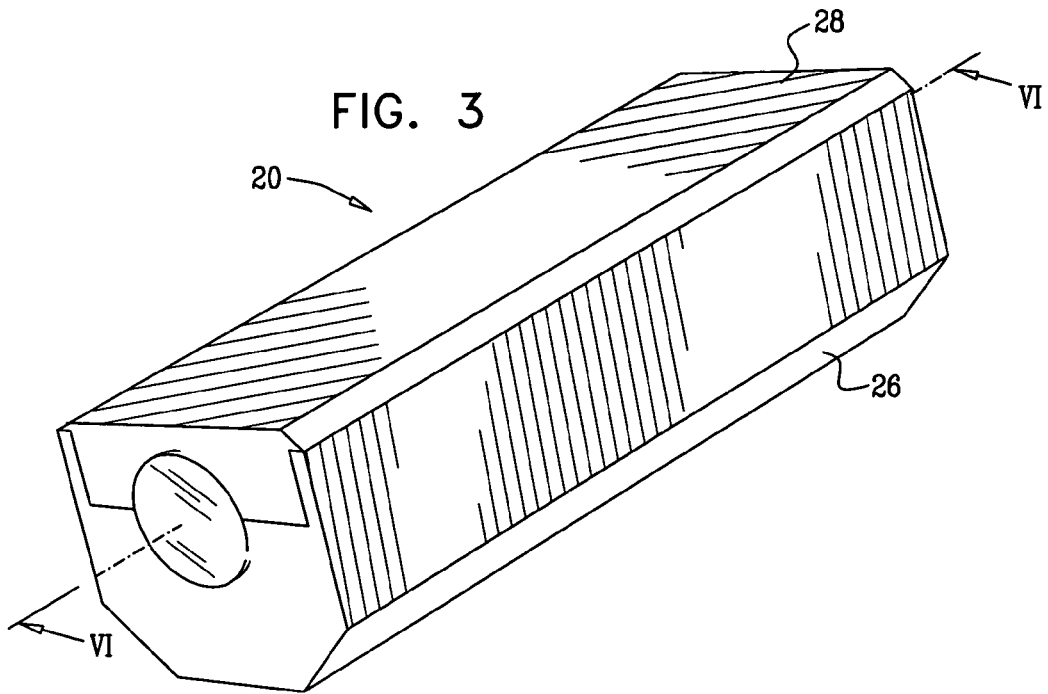
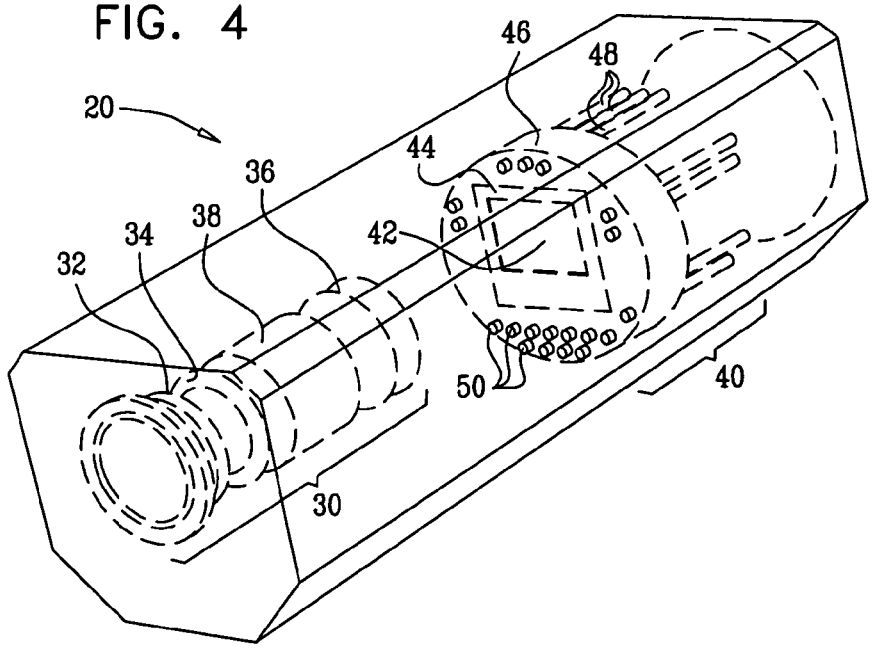

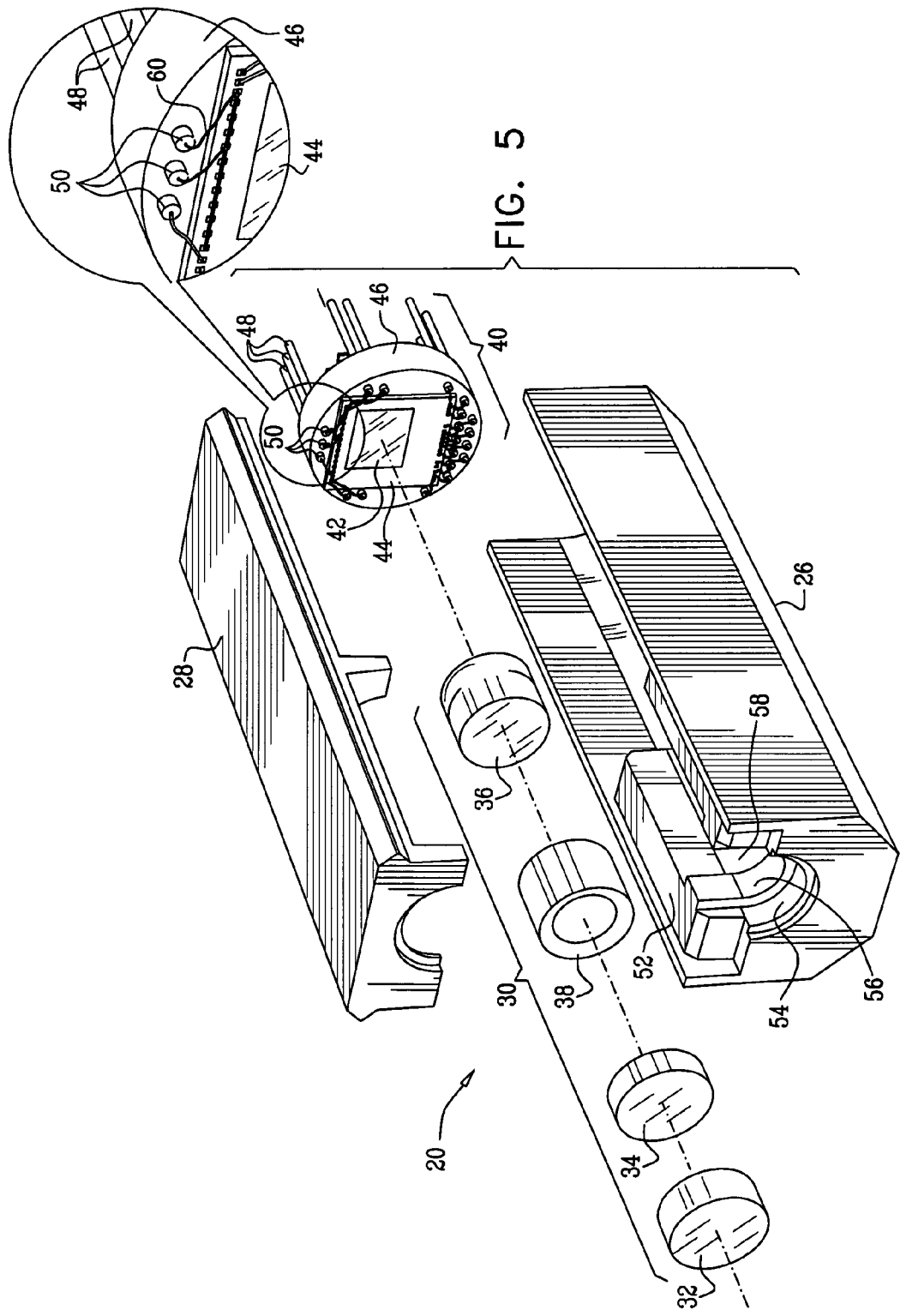

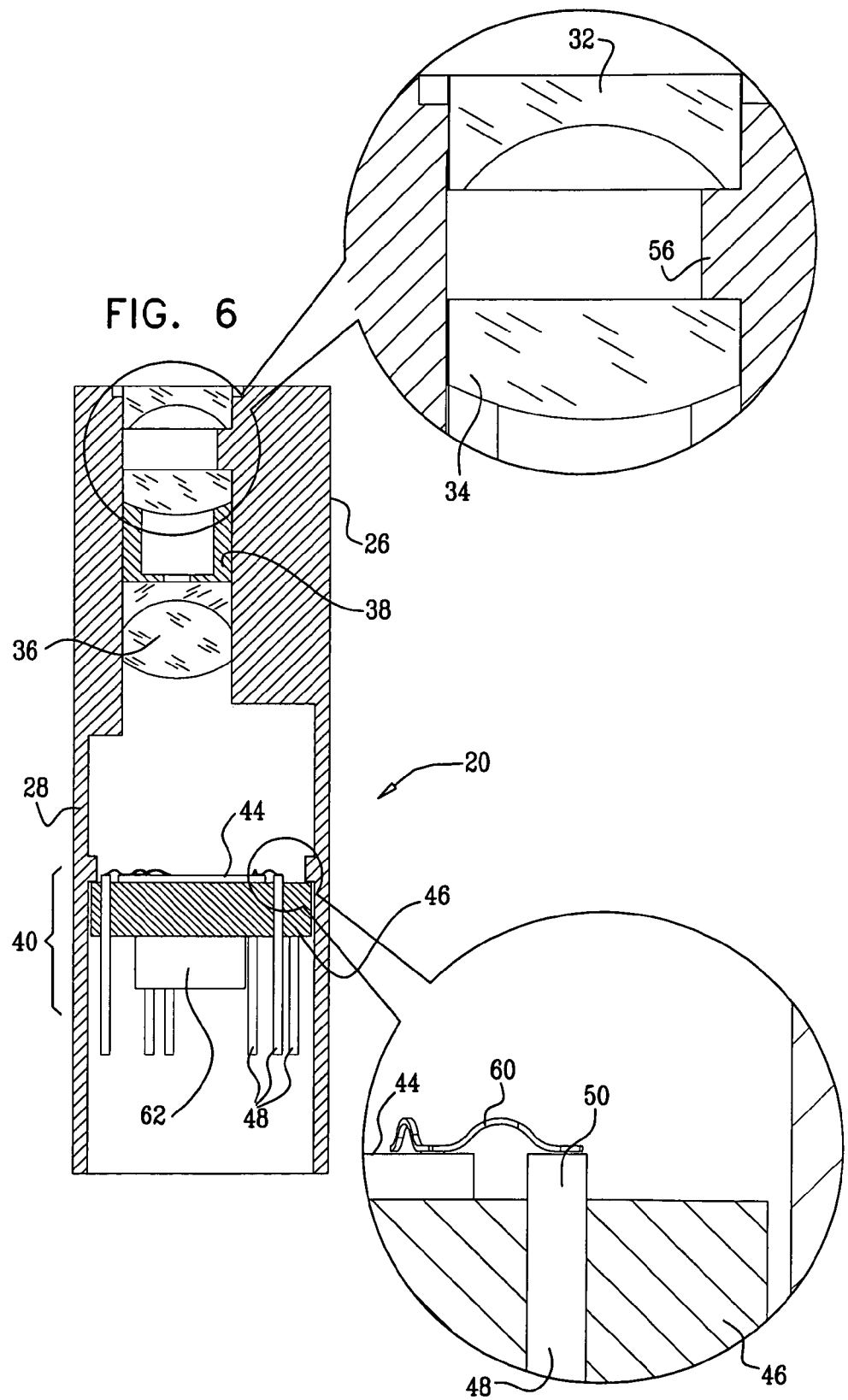

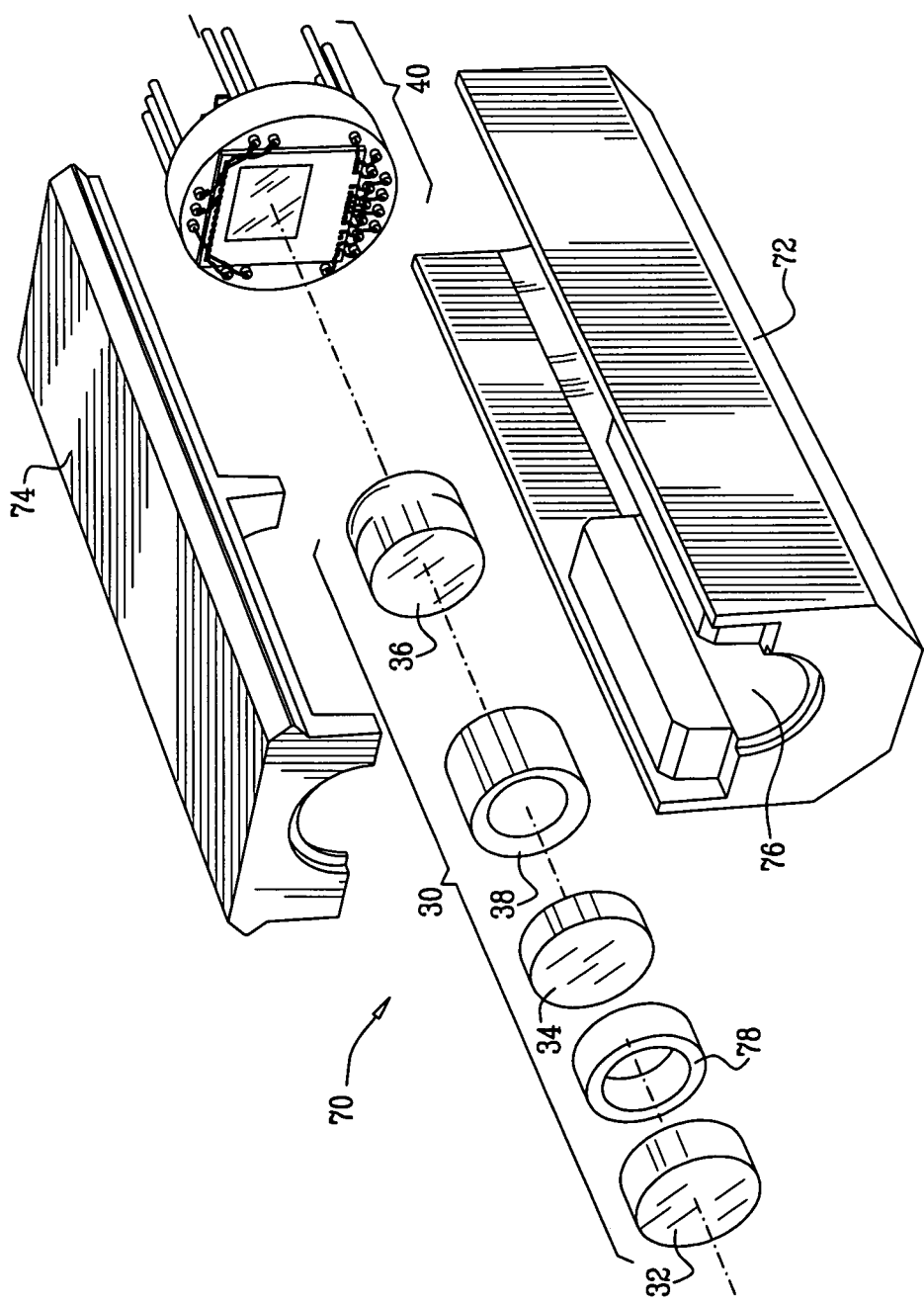

IMAGING SYSTEMS AND METHODS, PARTICULARLY FOR USE WITH MEDICAL INSTRUMENT USED IN OPEN SURGERY

RELATED APPLICATIONS

This application claims the benefit of and priority to U.S. Provisional Application Ser. No. 60/912,337, filed Apr. 17, 2007, entitled METHODS AND INSTRUMENTS FOR IMAGING IN MEDICAL OR SURGICAL PROCEDURES and U.S. Provisional Application Ser. No. 61/016,557, filed Dec. 24, 2007, entitled COMPACT CAMERA, the contents of which are hereby incorporated by reference as if recited in full herein for all purposes.

BACKGROUND

This inventive subject matter generally relates to imaging systems and methods for surgical or other medical procedures. More particularly, it relates to compact imaging systems for use on instruments for open surgery.

When a surgeon is performing an open surgery, the area of interest may be too small for more than one surgeon to observe. Or the area of the surgical table may be too crowded and not easily viewed by other medical personnel who may be interested in viewing the surgical site and procedure. Some surgical rooms have overhead cameras that allow others to view a surgical site, but the movement of persons around the table and angle of viewing may preclude a view of the area of interest. Accordingly, there is a need for improved imaging systems and methods of dissemination of imaging data that facilitate collaboration, participation, and surgical and medical training.

There are several types of surgery. The first is endoscopic surgery, such as laparoscopic surgery, in which a small incision is made in order to insert working instruments and an endoscopic viewing instrument. Imaging systems for endoscopic surgery are well known and are typically located either on the distal end of the insertion portion of an instrument or on its proximal end (using rod lens or fiber based endoscope). A second type of surgery is endoluminal (natural orifice) surgery, in which no external incision is required. U.S. Pat. No. 4,905,670, by Adair, discusses a cervical speculum with a clip-on camera, and therefore belongs to this second category of surgery. Other prior art includes U.S. Pat. Nos. 5,667,473, 5,667,478 and 5,735,792. In these patents, the instruments are endoscopic instruments rather than instruments for open surgery, and one or more optical fibers are run along the instruments in order to view the surgical site without the need for a separate endoscope.

A third type of surgery is open surgery, in which a larger incision is made in order to view the site directly and to maneuver the working instruments. This type of surgery can be observed without an insertion of an imaging system.

Although many video cameras and imaging systems have been developed for endoscopic applications, the range of video imaging systems for open surgical applications is much more limited. For example, some operating rooms have overhead cameras, but the view provided by the camera may be blocked by the hands or instruments of the surgical personnel. Furthermore, the camera may not have sufficient magnification to give observers and other members of the surgical team a clear picture of the surgical site.

Accordingly, the prior art does not disclose or suggest imaging systems or methods that are suitable for use in the viewing environment of open surgery. Nor does the prior art disclose methods for extending the audience in open surgery or methods of dissemination of the imaging data or methods of collaboration in response to imaging data.

SUMMARY

The inventive subject matter overcomes problems in the prior art by providing a camera system and methods with the following qualities, alone or in combination:

In certain respects, the inventive subject matter is directed to permanently or removably mounted cameras that are mounted on a non-insertion portion of a medical instrument, and to methods of making and using the same. The medical instrument with associated camera may be used in open surgery. Open surgery is a method of surgery in which an incision is made to enable direct viewing of and access to the surgical site, an instrument is introduced into the surgical site, and a camera attached to or integrated in the instrument is used to provide a displayed image in addition to the direct viewing of the site by the surgeon. Some times structural pathology prevents direct visualization, and the only means to see the operated site would be through a camera mounted on a tool. By placing the camera on the instrument, the site of interest may be kept in clear, direct view, unobstructed by hospital personnel or objects. Accordingly, the inventive subject matter allows for better-informed judgments from consulting personnel, such as specialist physicians or surgeons, or for better training of students in an educational setting, for example. The inventive subject matter is particularly advantageous at allowing participation of remotely located persons, who may be participating via a telecommunications or data network.

Various methods are within the scope and contemplation of the inventive subject matter. For example, in one possible embodiment, the inventive subject is directed to a method of imaging in open surgery comprising providing an instrument with an associated imaging system and acquiring imaging data with the camera and presenting it on a presentation device, such as a computer monitor, television, or via a printer.

In another possible embodiment, the inventive subject matter is directed to a method of communicating imaging data comprising providing a medical instrument, the instrument comprising a distally disposed working portion for working in a surgical or medical procedure, and a proximally disposed non-working portion having an associated imaging system, the non-working portion being on a non-insertion portion of the instrument.

In other embodiments, the inventive subject matter is directed to a compact video camera that is particularly suited to give a close, unobstructed view of the surgical site in open surgery. The camera may be attached to a shaft of a surgical instrument so as to image the area of the working element at the distal end of the instrument. The camera may be self-contained, requiring no intervening fiberoptics or modification of the instrument to which it is to be attached.

In some embodiments, the camera is produced using novel components and methods of manufacture that facilitate small size, high reliability and low cost. Although the camera is described below with particular reference to surgical applications, the novel features that are described below may similarly be implemented in cameras and imaging systems for other uses.

In another possible embodiment, the inventive subject matter is directed to an electronic imaging apparatus, comprising: a chassis, having an open cylindrical groove formed therein; an image sensor assembly mounted in the chassis, the image sensor assembly comprising an electronic image sensor; a plurality of lenses, which are fitted into the groove in respective positions so as to form an image on the image sensor; and a cover, which closes over the image sensor assembly and the lenses in the chassis.

In another possible embodiment, the inventive subject matter is directed to a method for producing a camera, comprising: providing a chassis having an open cylindrical groove formed therein; mounting in the chassis an image sensor assembly comprising an electronic image sensor; fitting a plurality of lenses into the groove in respective positions so as to form an image on the image sensor; and closing a cover over the image sensor assembly and the lenses in the chassis.

In another possible embodiment, the inventive subject matter is directed to a camera for a surgical instrument, comprising: a chassis having an open cylindrical groove formed therein, an image sensor assembly, which comprises an electronic image sensor and is disposed in the chassis, a plurality of lenses that are fitted into the groove in respective positions so as to direct an image onto the image sensor; a cover, which closes over the image sensor assembly and the lenses in the chassis; the camera having means for connecting to a shaft portion of a predetermined surgical instrument, comprising: a distally disposed working portion for working in a surgical or medical procedure, and a proximally disposed non-working portion, the non-working portion being on a non-insertion portion of the instrument; and wherein the chassis has a compact shape so as not to substantially impede the use of the surgical instrument, which shape includes a length not exceeding the length of the non-working portion of the surgical instrument and a width or diameter not exceeding about 3 times the width or diameter of the shaft portion.

In the embodiments of methods, systems, and apparatuses disclosed herein, there may be one or more spacers that are located in the groove between the lenses; at least one of the spacers may be fitted into the groove together with the lenses; one of the spacers may be a step that is built into the groove; the groove may be hemi-cylindrical; the image sensor assembly may comprise a non-conducting substrate, which has front and back sides and comprises through-wires molded into the substrate so as to pass through the substrate from the front side to the back side, wherein the image sensor is fixed to the front side of the substrate and is electrically connected to the through wires at the front side of the substrate; the connecting means may be a clip for fastening the camera onto the shaft; there may be a solid-state light source for illuminating a surgical site; the imaging system's image sensor may be a CMOS or CCD image sensor; there may be a communications interface for communicating imaging data to a remote location.

These and other embodiments are described in more detail in the following detailed descriptions and the figures. The foregoing is not intended to be an exhaustive list of embodiments and features of the present inventive subject matter. Persons skilled in the art are capable of appreciating other embodiments and features from the following detailed description in conjunction with the drawings.

BRIEF DESCRIPTION OF THE DRAWINGS

The following figures show embodiments according to the inventive subject matter, unless noted as showing prior art.

FIG. 3 is a schematic, pictorial illustration of a video camera usable with a medical instrument for open surgery;

FIG. 4 is a schematic, transparent view of the video camera of FIG. 3;

FIG. 5 is a schematic, exploded view of the video camera of FIG. 3;

FIG. 6 is a schematic, sectional view of the video camera of FIG. 3;

FIG. 7 is a schematic, exploded view of a video camera, in accordance with another embodiment of the inventive subject matter.

DETAILED DESCRIPTION

Figure 1:
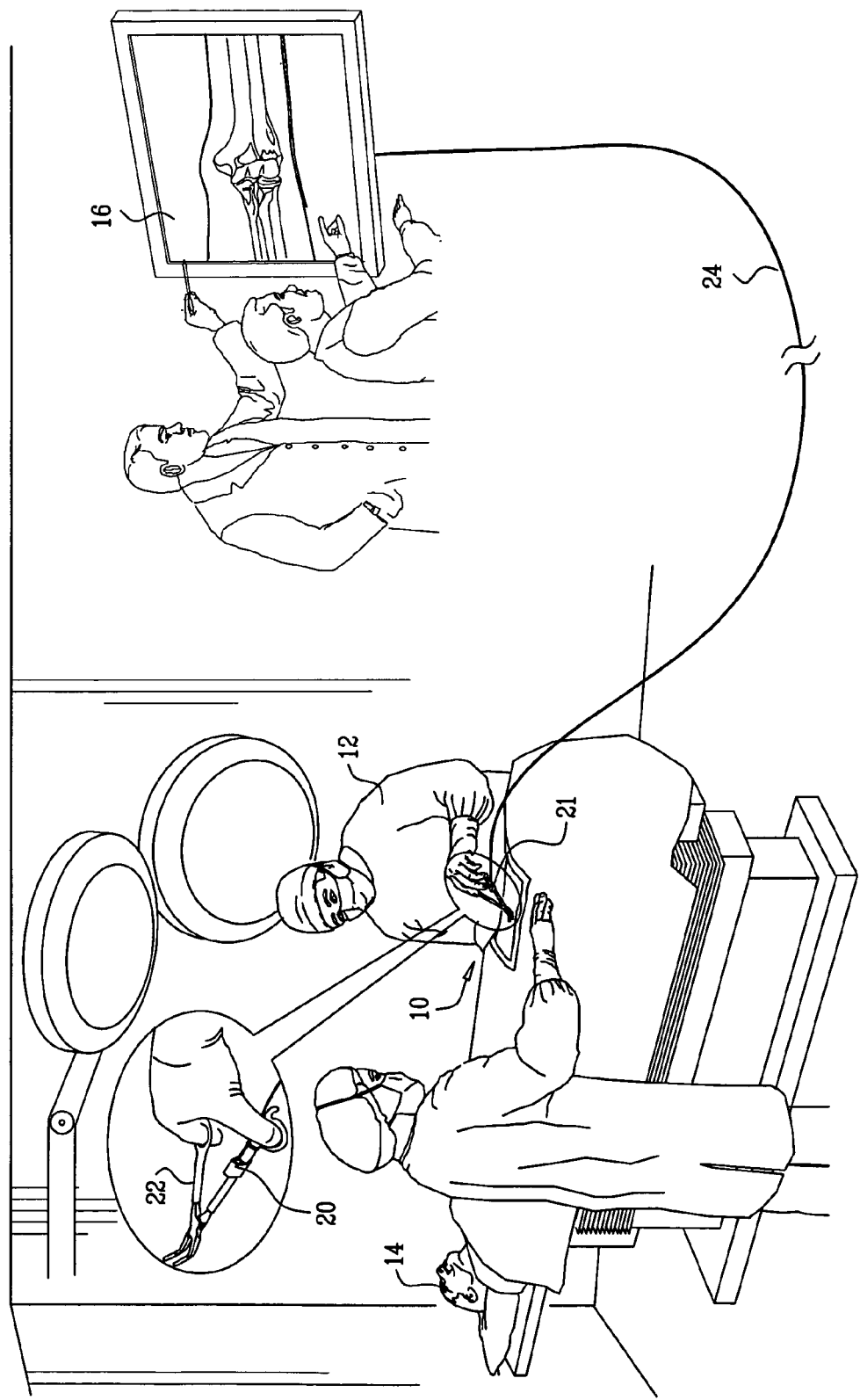
FIG. 1 is a schematic, pictorial view of a system for surgery using an instrument of open surgery with an integrated, compact camera.

Representative embodiments according to the inventive subject matter are shown in FIGS. 1-8.

In a most general sense, the inventive subject matter is directed to the use of an imaging system. As used herein, "imaging system" typically means an objective optic element or elements and a device on which the objective optics convey the image for capture. There are many known cameras that are representative of imaging systems. The imaging system illustrated in the figures is an electronic imaging system comprising an objective lens and a pixellated, electronic image sensor, such as a CCD or CMOS sensor.

The imaging system may capture an image in an open surgical procedure to provide additional viewing opportunities beyond the restricted view generally presented to only the operating surgeon.

The camera may be attached, integrated in, or otherwise connected to one of the instruments used in the operation in such a way that it will not complicate any technical procedure done by the instrument from one end, and will allow anyone in the operating room, or in a remote location, to see the working area from a different angle or point of view on a monitor or other through another output device, such as printer. As used herein, an instrument "associated" with a camera means an instrument with a camera that is physically coupled to the instrument, in a removable or non-removable manner, such as by mounting or attaching the camera on or within a known instrument or making an instrument with an integrated camera feature on or in the instrument.

Typically, the instrument on which the imaging system is associated will have a distally disposed working portion for working in a surgical or medical procedure, and a proximally disposed non-working portion having an associated imaging system, the non-working portion being on a non-insertion portion of the instrument. As used herein, "non-insertion portion" means a portion that is generally kept above the plane of a body surface; however, if there is a wide opening or recess below the plane, the non-insertion portion may be used below the plane of the body surface, if such use is consistent with open-type surgery.

The camera may be configured with a battery or coupled to a remote power source. The power source may be the same one associated with a medical instrument with which the camera is mounted or otherwise used. The camera may be configured with a configuration for wireless transmission of image data to a received, such as camera control unit (CCU), such communication interfaces including hardware and/or software components and protocols, as are well known to persons skilled in the art.

In some embodiments the camera and/or the instrument may be disposable in the context of the medical arts, namely a camera intended for one time use. As used herein, "camera" means a video or still camera.

Generally, known camera systems may be adapted for use in the inventive subject matter. Example systems are disclosed in WO2006066022, US2006173242 and US20050250983 which are hereby incorporated by reference in their entireties. Other known systems that have a form that may be adapted for use in the inventive subject matter disclosed herein include capsule-form endoscopic cameras, such as those disclosed in US2006253004 and US2006004256, which are hereby incorporated by reference in their entireties.

The following sections provide details of an illustrative camera system according to the inventive subject matter. The examples are strictly for illustrative purposes and are not intended to be limiting of the scope of the inventive subject matter, unless specifically indicated to such (as well as equivalents) in a claim now or in the future appended hereto.

Figure 2:
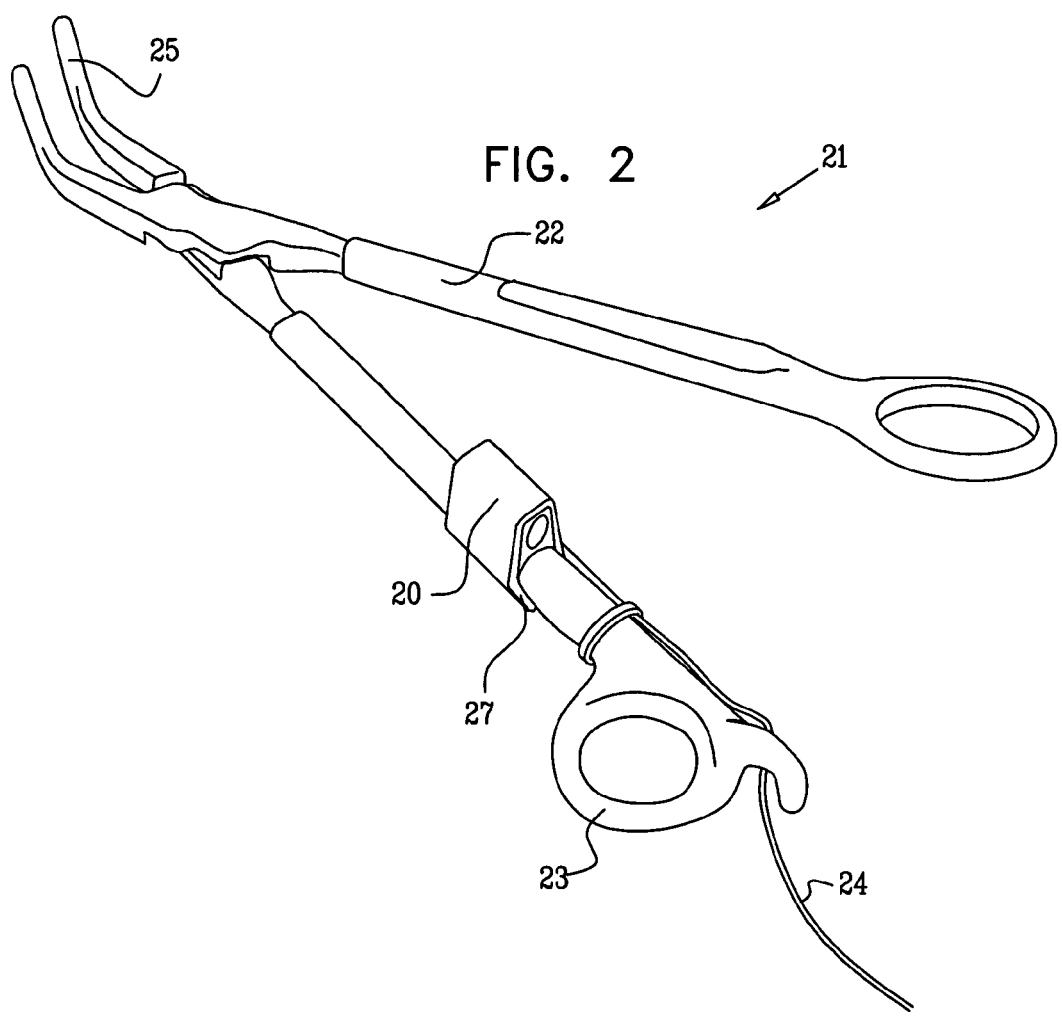
FIG. 2 is a schematic, pictorial illustration of a video camera attached to a medical instrument.

FIGS. 1 and 2 schematically illustrate a system 10 for surgery, in accordance with an embodiment of the present invention. FIG. 1 shows a surgeon 12 operating on a patient 14 in open surgery, using a surgical instrument 21. FIG. 2 is a pictorial illustration of instrument 21 showing a miniature camera 20, which is attached to a shaft 22 of the instrument. The term "shaft" as used herein generally means a portion of the instrument between a proximal end 23 of the instrument, which is typically grasped by the operator, and a working element 25 at the distal end. The shaft typically comprises an elongate structure proximal to the working element. The shaft may be cylindrical, as in FIG. 2, but may alternatively have any other suitable profile. The shaft itself may be configured to provide space to house a camera. Alternatively, camera 20 may be attached to shaft 22 by a suitable connecting means, such as a clip 27, or alternatively by any other suitable sort of fastening, such as a screw, adhesives or adhesive strips, straps, hook/loop fasteners (e.g., Velco™). The attachment may be such that the camera may be removed and attached to other instruments, or it may be fixed and substantially permanent.

Camera 20 is positioned, as can be seen in the figures, to capture images of an area in the vicinity of working element 25 within the body of patient 14. The camera may have a communications interface for communicating with remote systems. For example, a cable 24 conveys signals from the camera to a video console and display 16. Typically, during use of instrument 21 in open surgery, surgeon 12 makes an incision in the patient's body to provide direct access to the surgical site. The surgeon inserts working element 25 through the incision into the patient's body, while holding proximal end 23 outside the body, and uses the working element in operating on tissue in the body. Camera 20 may remain outside the body during the procedure. At the end of the procedure, the surgeon closes the incision.

In contrast to endoscopic procedures, working element 25 in open surgery generally remains directly visible to the surgeon during the surgery. On the other hand, other members of the surgical team, as well as observers, may be unable to see the area of the working element because their view is blocked by the surgeon himself or by other objects or personnel. These team members and observers are able to observe the images captured by camera 20 on display 16 in real time. The display may be at a location remote from the patient, including locations in the operating room that are not directly adjacent to the operating table, as well as locations in other rooms or buildings.

Additionally or alternatively, the output of camera 20 may be transmitted over a communications network or fed to a video recorder or other video processing equipment (not shown). The image data produced by the camera may be used in various ways, including medical or surgical training; participation or collaboration in the surgical procedure in progress or in a subsequent procedure on the same patient; review of recorded procedures; editing, enhancement, image extraction or other modifications on the image data; archiving; and ensuring compliance with rules or policies, such as in regulatory submissions.

In open surgery there is generally sufficient light cast by overhead lamps and, in some cases, by the surgeon's headlamp to permit camera 20 to capture clear images without supplemental lighting. Optionally, camera 20 may also comprise an integrated light source, such as a suitable light-emitting diode (LED), for illuminating the area under view. Alternatively, a separate light source may be attached to one of the shafts of instrument 21. (These optional additional light sources are not shown in the figures.)

FIGS. 3-6 schematically show details of camera 20, in accordance with an embodiment of the present invention. FIG. 3 is a pictorial external view of the camera, while FIG. 4 shows some of the internal elements of the camera in a transparent view. FIG. 5 is an exploded view, and FIG. 6 is a sectional view taken in a vertical plane containing the line VI-VI in FIG. 3. Insets in FIG. 6 also show enlarged views of certain details of the construction of the camera.

The components of camera 20 are contained in a case, which comprises a chassis 26 that is closed by a cover 28. For the application illustrated in FIG. 2, for example, the case may have an outer diameter of approximately 5 mm and a length of 15 mm, but larger or smaller dimensions are also possible depending on application requirements. Chassis 26 contains a lens assembly 30, which forms an image of the area of interest on a sensor assembly 40. The sensor assembly comprises an electronic image sensor 44, such as a pixellated CCD or CMOS integrated circuit device comprising an array 42 of sensor elements. In the configuration shown in FIG. 2, lens assembly 30 may have a total field of view of about 60° in the object space, with a working distance (depth of field) from 100 to 250 mm, but other optical configurations may alternatively be used as appropriate.

Lens assembly 30 in this example comprises lenses 32, 34 and 36. These lenses typically have a diameter of about 2 mm or less. Accurate assembly of such small optics to within design tolerances is understandably difficult when conventional methods of assembly are used. Typically, careful alignment and testing are required to ensure that the lenses are properly positioned.

In camera 20, however, for ease and accuracy of assembly, chassis 26 comprises a lens holder 52, which has an open cylindrical groove 58 for receiving the lenses. In the context of the present patent application and in the claims, the term "open cylindrical groove" refers to a groove having the shape of an inner surface of a cylinder but extending in angle around only part of the circumference of the cylinder, leaving an opening at one side of the cylinder for insertion of the lenses. The groove may advantageously be hemi-cylindrical, as illustrated in the figures. The groove is shaped and sized precisely to receive the lenses. Proper spacing between the lenses, in accordance with the optical design of assembly 30, is maintained by spacers 38 and 56. These spacers may be separate components, such as spacer 38, that are inserted into groove 58, or they may alternatively be built into the groove, as is spacer 56, in the form of a step in the groove diameter. Spacer 56 effectively creates a slot 54 for accommodating lens 32.

Thus, all that is necessary to assemble optical assembly 30 in camera 20 is to fit lens 32 into slot 54, and to fit lenses 34 and 36, separated by spacer 38, into groove 58 behind spacer 56. Alternatively, spacer 38 may be replaced by a fixed, built-in step like spacer 56. Lens holder 52 is produced with sufficient accuracy so that the lenses, once inserted in this manner, are in the proper positions without requiring additional alignment or testing. The lenses may be glued into the lens holder in these positions. When cover 28 is then closed over chassis 26, it holds the lenses securely in place.

Image sensor 44 is mounted on a non-conducting substrate 46. To minimize the diameter of camera 20, it is desirable that the diameter of substrate 46 be as small as possible, while still containing sufficient through-wires 48 to convey the necessary signals to and from sensor 44. For this reason, the inventors have found it advantageous to make substrate 46 from glass, with through-wires 48 molded into the glass at the time of fabrication of the substrate. In other words, instead of drilling vias through the substrate and then filling the vias with metal, as is common in methods of printed circuit production that are known in the art, through-wires 48 are held in place while substrate 46 is molded, so that no subsequent drilling is required. As a result, the through-wires may have narrow diameter, typically on the order of 100 μm, and may be spaced close together without compromising the strength and integrity of the substrate.

To produce sensor assembly 40, image sensor 44 is aligned and fixed to the front side of substrate 26, using a suitable glue, for example. The image sensor is then connected to wires 48 by bonding fine wires 60 between contact pads (not shown) on sensor 44 and forward ends 50 of wires 48, which are typically cut so as to protrude slightly above the surface of substrate 46. Alternatively, printed circuit traces (not shown) may be formed on the front side of the substrate to connect the sensor to wires 48. The rear ends of wires 48, at the back side of substrate 46, are connected to the appropriate conductors in cable 24 (FIG. 2). Optionally, one or more additional circuit components 62 may be attached to the back side of the substrate and connected to wires 48 by wire bonding or printed circuit traces.

As shown in FIGS. 5 and 6, the shape and inner diameter of chassis 26 are chosen so that substrate 46 fits snugly into the chassis. Thus, to complete the assembly of camera 20, the assembled sensor assembly 40 is mounted in the chassis and is aligned so that lens assembly 30 casts a focused image onto array 42. The substrate is then glued or otherwise fastened in place, and cover 28 is closed over the lens assembly and sensor assembly. Clip 27 (FIG. 2) may be added (to either chassis 26 or cover 28), and the camera is ready for use.

The use of a substrate with molded-in through-wires is advantageous not only for mounting image sensors, but also for mounting other types of circuit components in narrow spaces. Although substrate 46 is described above as comprising glass, other types of non-conducting moldable materials, such as certain plastics, may alternatively be used for this purpose.

Figure 8:
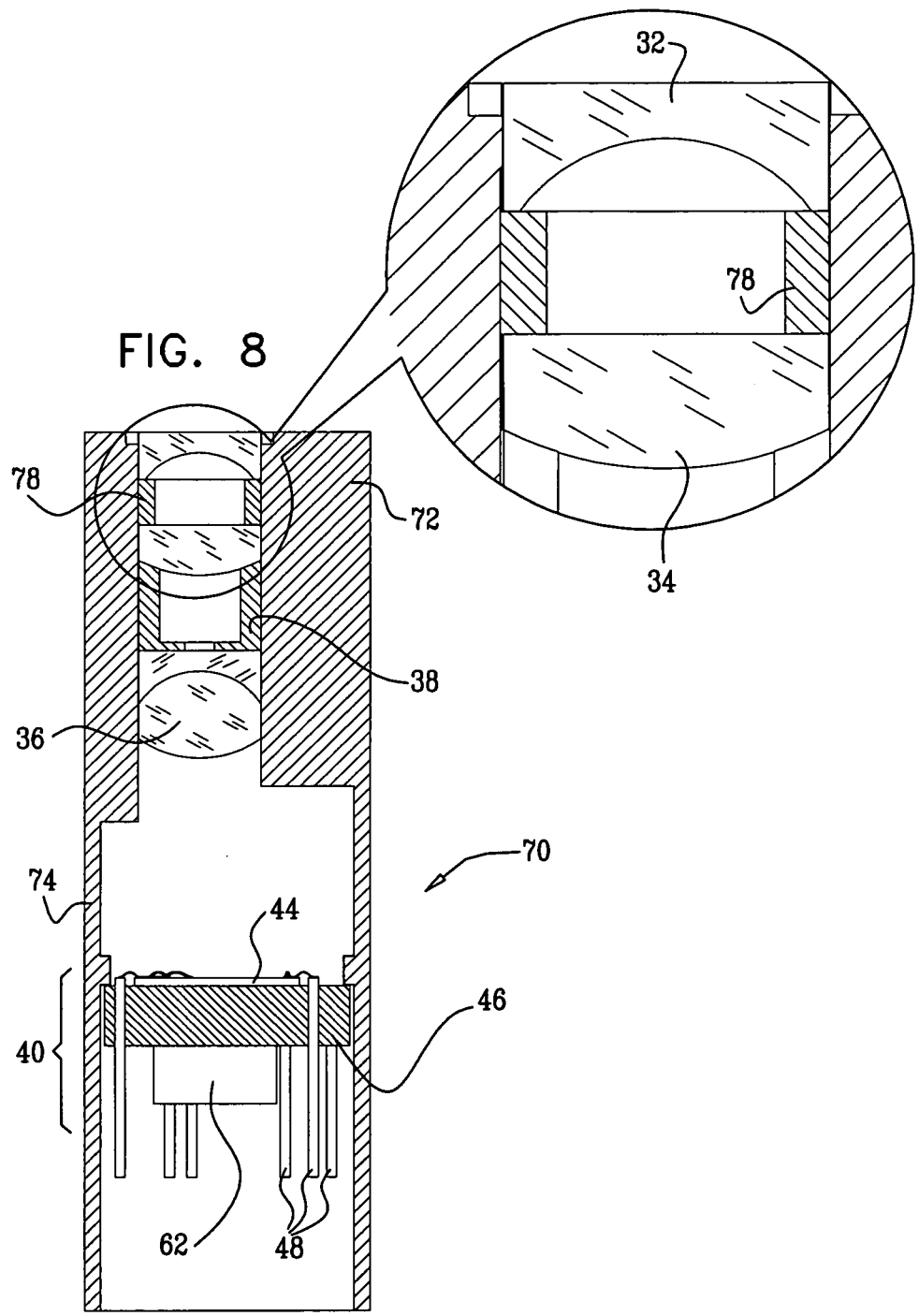
FIG. 8 is a schematic, sectional view of the video camera of FIG. 7.

FIGS. 7 and 8 schematically illustrate a camera 70, in accordance with an alternative embodiment of the present invention. FIG. 7 is an exploded view, while FIG. 8 is a sectional view, similar to the views of camera 20 shown in FIGS. 5 and 6. Camera 70 includes a chassis 72 and cover 74, as well as other optical and image sensing components as in camera 20. Chassis 72, however, comprises a lens holder 76 that contains a smooth open cylindrical groove, without built-in spacers. Instead, the optical assembly in camera 70 uses an additional spacer 78 between lenses 32 and 34. This arrangement simplifies the manufacture of chassis 72, at the expense of minor additional complication in assembly of the camera.

Although cameras 20 and 70 are described hereinabove with particular reference to surgical system 10 and instrument 21, the principles of the design and construction of these cameras may similarly be applied in other imaging applications, and particularly applications that require a very compact camera. By the same token, although the method of intra-operative video imaging for open surgery that is illustrated in FIGS. 1 and 2 is described with specific reference to camera 20, miniature video cameras of other types may likewise be attached to the shaft of a surgical instrument for the purposes of this method. Furthermore, instrument 21 itself is shown purely for the sake of illustration, and cameras may also be attached in this fashion to surgical instruments of other types.

In one possible embodiment, the inventive subject matter is directed to a camera for a surgical instrument wherein the camera has a compact shape so as not to substantially impede the use of the surgical instrument, which shape includes a length not exceeding the length of the non-working portion of the surgical instrument to which the camera is associated and a width or diameter not exceeding about 3 times the width or diameter of the shaft portion of the instrument to which the camera is mounted or otherwise associated.

METHODS OF USE

Various methods are within the scope and contemplation of the inventive subject matter. For example, in one possible embodiment, the inventive subject is directed to a method of imaging in open surgery comprising providing an instrument with an associated imaging system and acquiring imaging data with the camera and presenting it via a standard data communications interface to a presentation device, such as a computer monitor, television, or via a printer.

In another possible embodiment, the inventive subject matter is directed to a method of open surgery that includes the steps of: making an incision in a patient to provide direct access to a surgical site; introducing a surgical instrument to the surgical site, the surgical instrument comprising a tissue treatment portion for the modification or manipulation of tissue at the surgical site, and a non-working portion proximal from the tissue treatment portion, and an imaging system associated with the non-working portion; displaying an image of the surgical site obtained from the imaging system; modifying or manipulating the tissue at the surgical site by means of the surgical instrument; and closing the incision in the patient at the end of the surgical procedure. The steps of this and other methods described herein need not be performed in the exact order listed. For instances the displaying of the image step may be performed, for example, after the modification or manipulation of the tissue, as well as before it.

In another possible embodiment, the inventive subject matter is directed to a method of open surgery that includes the steps of: making an incision in a patient to provide direct access to a surgical site; introducing a surgical instrument to the surgical site, the surgical instrument comprising a tissue treatment portion for the modification or manipulation of tissue at the surgical site, and a non-working portion proximal from the tissue treatment portion, and an imaging system associated with the no-working portion acquiring an image of the surgical site in the form of image data using the imaging system; modifying or manipulating the tissue at the surgical site by means of the surgical instrument; and closing the incision in the patient at the end of the surgical procedure.

In another possible embodiment, the inventive subject matter is directed to a method of communicating imaging data comprising providing a medical instrument, the instrument comprising a distally disposed working portion for working in a surgical or medical procedure, and a proximally disposed non-working portion having an associated imaging system, the non-working portion being on a non-insertion portion of the instrument; and transmitting the imaging data to a location remote from the surgical table for viewing or use by others who are beyond the immediate area of the surgical table (or other platform). "Beyond the immediate area of the surgical table," generally means an area that is sufficiently far from the surgical table that viewing of the details of the surgical site are obscure or blocked to the naked eye In the foregoing embodiments, imaging system may be removably mounted on the instrument; the imaging system may comprise a pixellated imaging sensor, such as a CCD or CMOS sensor; and/or the instrument may include a solid state light source, such as an LED for illuminating the a site of interest.

In the foregoing embodiments, the data representing acquired images may be communicated to a display device and presented (e.g., on a computer or television monitor or via a printer) in substantially real time to one or more persons beyond the adjacency of a patient support for the patient with the site of interest; the one or more persons are not in the same room as the patient; and/or the data is communicated via a digital data or telecommunications network. Representative examples of such networks include LANs, WANs, Intranets, and the Internet.

In the foregoing embodiments, the data representing acquired images may be communicated to a data storage medium for on-demand presentation to a viewer.

In the foregoing embodiments, the data may be used in one or more of the following respects: medical or surgical training; participation or collaboration in the medical procedure being performed; participation or collaboration in a medical procedure for the same patient subsequent to the one being performed; modification of the imaging data, such as to provide editing, enhancements or derivations; archiving of procedures; for compliance with established rules or policies; for use in regulatory submissions.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

All patent and non-patent literature cited herein is hereby incorporated by references in its entirety for all purposes.

Currently claimed inventions:

1. An electronic imaging apparatus, comprising:
   an image sensor assembly, which includes an electronic image sensor;
   a plurality of lenses, which include an optical axis that forms an image on the electronic image sensor;
   a chassis, comprised of at least three sides that create an internal groove, a proximal open end, a distal open end, an open top, and a lens holder at the distal open end, wherein the internal groove comprises a cylindrical inner surface for positioning of the plurality of lenses and the image sensor assembly and an opening extending through the groove configured for insertion of the plurality of lenses and the image sensor assembly transversely relative to the optical axis, wherein the plurality of lenses are inserted into the lens holder, wherein the lens holder has an open cylindrical groove and is located near the distal open end and the image sensor assembly is located near the proximal open end; and
   a cover having a cylindrical inner surface, which covers the open top and closes over the image sensor assembly and the plurality of lenses, holding the plurality of lenses securely in their respective positions in the chassis.

2. The apparatus of claim 1, wherein one or more spacers are positioned in the open cylindrical groove between the plurality of lenses.

3. The apparatus of claim 2, wherein at least one of the one or more spacers is fitted into the open cylindrical groove together with the plurality of lenses.

4. The apparatus of claim 2, wherein at least one of the one or more spacers comprises a step that is built into the lens holder.

5. The apparatus of claim 1, wherein the cylindrical inner surface is hemi-cylindrical.

6. The apparatus of claim 1, wherein the image sensor assembly comprises a non-conducting substrate, which has front and back sides and comprises through-wires molded into the substrate so as to pass through the non-conducting substrate from the front side to the back side, wherein the electronic image sensor is fixed to the front side of the non-conducting substrate and is electrically connected to the through wires at the front side of the non-conducting substrate.

7. The apparatus of claim 1, further comprising a solid-state light source for illuminating a surgical site.

8. The apparatus of claim 7, further comprising a communications interface for communicating imaging data to a remote location.

9. The apparatus of claim 1, wherein the electronic image sensor comprises a CMOS or CCD image sensor.

10. The apparatus of claim 1, further comprising a communications interface for communicating imaging data to a remote location.

11. The apparatus of claim 1, wherein the chassis is configured to be removably mountable to a proximally disposed non-working portion of a medical instrument.

12. The apparatus of claim 1, wherein the internal groove comprises each shape for the plurality of lenses and for the image sensor assembly.

13. A camera for a surgical instrument, comprising:
   an image sensor assembly, which includes an electronic image sensor and is disposed in a chassis;
   a plurality of lenses, which include an optical axis that directs an image onto the electronic image sensor;
   the chassis comprised of at least three sides that create an internal groove, a proximal open end, a distal open end, an open top, and a lens holder at the distal open end, wherein the internal groove comprises a cylindrical inner surface for positioning of the plurality of lenses and the image sensor assembly and an opening extending through the groove configured for insertion of the plurality of lenses and the image sensor assembly transversely relative to the optical axis, wherein the plurality of lenses are inserted into the lens holder, wherein the lens holder has an open cylindrical groove and is located near the distal open end and the image sensor assembly is located near the proximal open end; and
   a cover having a cylindrical inner surface, which covers the open top and closes over the image sensor assembly and the plurality of lenses, holding the plurality of lenses securely in the chassis;

the camera having means for connecting to a shaft portion of the surgical instrument comprising:
- a distally disposed working portion for working in a surgical or medical procedure, and a proximally disposed non-working portion, the non-working portion being on a non-insertion portion of the surgical instrument; and
- wherein the chassis has a compact shape so as not to substantially impede the use of the surgical instrument, wherein the compact shape includes a length not exceeding the length of the non-working portion of the surgical instrument and a width or diameter not exceeding about 3 times the width or diameter of the shaft portion, wherein the camera is connected to the non-working portion of the surgical instrument.

14. The camera of claim 13, wherein the means for connecting comprises a clip for fastening the camera onto the shaft.

15. The camera of claim 13, further comprising a solid-state light source for illuminating a surgical site.

16. The camera of claim 13, wherein the electronic image sensor comprises a CMOS or CCD image sensor.

17. The camera of claim 13, further comprising a communications interface for communicating imaging data to a remote location.

18. An electronic imaging apparatus, comprising:
- an image sensor assembly mounted in a chassis, the image sensor assembly including an electronic image sensor;
- a plurality of lenses, which include an optical axis that forms an image on the electronic image sensor;
- the chassis, comprised of at least three sides that create an internal groove, a proximal open end, a distal open end, an open top, and a lens holder at the distal open end, wherein the internal groove comprises a cylindrical inner surface for positioning of the plurality of lenses and the image sensor assembly and an opening extending through the groove configured for insertion of the plurality of lenses and the image assembly transversely relative to the optical axis, wherein the plurality of lenses are inserted into the lens holder, wherein the lens holder has an open cylindrical groove and is located near the distal open end and the image sensor assembly is located near the proximal open end; and
- a cover having a cylindrical inner surface, which covers the open to and closes over the image sensor assembly and the plurality of lenses, holding the plurality of lenses securely in their respective positions in the chassis, wherein the chassis is configured to be removably mountable to one or more medical instruments.

19. The electronic imaging apparatus of claim 18, wherein the open cylindrical groove is a groove having the shape of an inner surface of a cylinder but extending in angle around only part of the circumference of the cylinder, leaving an opening at one side of the cylinder for insertion of the lenses.

20. The electronic imaging apparatus of claim 18, wherein the chassis is configured to be removably mountable at other than a distal end of the one or more medical instruments.

\* \* \* \* \*

UNITED STATES PATENT AND TRADEMARK OFFICE
CERTIFICATE OF CORRECTION

| | |
|---|---|
| PATENT NO. | : 8,692,874 B2 |
| APPLICATION NO. | : 12/104406 |
| DATED | : April 8, 2014 |
| INVENTOR(S) | : Adler et al. |

It is certified that error appears in the above-identified patent and that said Letters Patent is hereby corrected as shown below:

In the Claims

Column 12, Line 16, delete "open to and", insert -- open top and --

Signed and Sealed this
Fifteenth Day of July, 2014

Michelle K. Lee
*Deputy Director of the United States Patent and Trademark Office*